United States Patent [19]
Stein

[11] Patent Number: 5,487,948
[45] Date of Patent: Jan. 30, 1996

[54] BIS(BIS-SILYLALKYL) DICARBOXYLATES AS ADHESION PROMOTERS AND COMPOSITIONS CONTAINING THEM

[75] Inventor: Judith Stein, Schenectady, N.Y.

[73] Assignee: General Electric Company, Schenectady, N.Y.

[21] Appl. No.: 378,692

[22] Filed: Jan. 26, 1995

[51] Int. Cl.$^6$ ............................................. B32B 9/04
[52] U.S. Cl. ......................... 428/447; 428/450; 556/440; 556/438; 524/730; 524/265; 524/267; 524/588; 524/733; 524/789; 524/779; 524/783; 524/785; 524/788
[58] Field of Search ........................ 556/440, 438; 524/730, 265, 267, 588, 733, 789, 779, 783, 785, 788; 428/447, 450

[56] References Cited

U.S. PATENT DOCUMENTS

| | | | |
|---|---|---|---|
| 3,759,968 | 9/1973 | Berger et al. | 556/440 |
| 3,773,817 | 11/1973 | Berger et al. | 556/440 |
| 3,808,248 | 4/1974 | Berger et al. | 556/440 |
| 5,164,461 | 11/1992 | Mitchell et al. | |

*Primary Examiner*—Melvyn I. Marquis
*Attorney, Agent, or Firm*—William H. Pittman

[57] ABSTRACT

Bis(bis-silylalkyl) dicarboxylates, especially maleates and fumarates, are prepared by a three-step process including esterification of malaic or fumaric acid or a functional derivative thereof with a branched dienol such as 1,6-heptadien-4-ol to form an alkadienol ester, reaction of the olefinic groups in said ester with a chlorosilane and alcoholysis of the chlorine atoms attached to silicon. The products are useful as adhesion promoters in addition curable polyorganosiloxane compositions.

13 Claims, No Drawings

BIS(BIS-SILYLALKYL) DICARBOXYLATES AS ADHESION PROMOTERS AND COMPOSITIONS CONTAINING THEM

BACKGROUND OF THE INVENTION

This invention relates to polyorganosiloxane compositions. More particularly, it relates to addition curable polyorganosiloxanes and still more particularly to materials having improved adhesion to plastic substrates.

The use of polyorganosiloxanes (hereinafter sometimes "silicones") in the form of elastomeric compositions is now widespread. Elastomeric silicones include room temperature vulcanizable compositions, which cure upon standing in the presence of moisture, and addition curable compositions, which cure rapidly upon heating.

Addition curable silicones are of particular use when rapid cure is desirable or when the presence of moisture or, ultimately, of the by-products formed during the curing of room temperature vulcanizable materials is not desired. Illustrative uses are as potting compounds, in sealed environments in which water is not tolerated or in electronic applications. Curing of the addition curable silicones may be by direct heating or by an equivalent means such as ultrasound.

Cured silicone elastomers prepared from addition curable compositions are frequently lacking in adhesion, especially to plastic substrates. Thus, improvement of their adhesion to plastics is very desirable.

U.S. Pat. No. 5,164,461 discloses the use of bis(3-methoxysilylalkyl) fumarate and maleate esters as adhesion promoters for addition curable silicones on both metal and plastic surfaces, described generically. It also describes the curing of such silicones at temperatures from 100° to 150° C. It has been found, however, that compositions containing these esters are difficult to cure at lower temperatures. Since substantially lower curing temperatures, frequently no higher than 85° C., are required in the case of many resinous and especially thermoplastic substrates to avoid heat-induced distortion, there is a need for alternative adhesion promoters which are effective for lower temperature curing after application of the silicones to plastic substrates.

The present invention includes a class of adhesion promoting esters for addition curable silicones which, when incorporated in said silicones, are effective with plastic substrates and at low curing temperatures.

Summary of the Invention

In one of its aspects, the invention includes bis(bis-silylalkyl) dicarboxylate esters having the formula

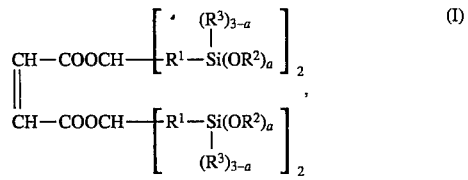

wherein $R^1$ is $C_{2-6}$ alkylene, each of $R^2$ and $R^3$ is independently $C_{1-8}$ alkyl and a is from 1 to 3, said esters being the cis- or trans-isomers or mixtures thereof.

Another aspect of the invention is addition curable compositions comprising a mixture of:

(A) at least one polyorganosiloxane having alkenyl groups bonded to silicon;

(B) at least one hydride polyorganosiloxane comprising at least one organosiloxane unit having an Si—H moiety;

(C) as a catalyst, at least one platinum group metal compound in an amount effective to cause hydrosilylation of reagent A with reagent B; and (D) an adhesion promoting proportion of a bis(bis-silylalkyl) dicarboxylate as described above.

Still another aspect is an article comprising a metal or plastic substrate having a coating of an addition curable composition as described above.

Detailed Description; Preferred Embodiments

The esters of formula I may be either cis- or trans-isomers; that is, they may be esters of maleic or fumaric acid. Fumaric acid is often preferred. The $R^1$ radicals therein are alkylene radicals having 2–6 and preferably 3 carbon atoms; i.e., the preferred value for $R^1$ is trimethylene. Each $R^2$ and $R^3$ radical is $C_{1-8}$ alkyl, preferably $C_{1-2}$ primary alkyl and most preferably methyl. The value of a is 1–3 and preferably 3.

Said esters may be prepared by a three-step process. The first step is esterification of maleic or fumaric acid or a functional derivative thereof (e.g., an acid chloride or anhydride) with a branched dienol such as 1,6-heptadien-4-ol to form an alkadienyl ester. The second step is reaction of the olefinic groups in said alkadienyl ester with a chlorosilane, preferably trichlorosilane, and the third step is alcoholysis of the chlorine atoms attached to silicon.

The esterification reaction may be conducted under conventional conditions, using a molar ratio of dienol to acid or functional derivative of at least 2:1 and preferably about 2.1–2.5:1. Particularly when the acid derivative is an acid chloride, it is frequently advantageous to incorporate in the reaction mixture an acid acceptor such as an amine-functionalized polymer. Examples of such polymers are pyridine-functionalized polystyrenes, which are commercially available.

After completion of the esterification reaction and removal of any excess dienol, reaction with the chlorosilane may be undertaken. It is ordinarily conducted under ambient conditions in the presence of a hydrosilylation catalyst, typically a platinum group catalyst.

By "platinum group" is meant the portion of Group VIII of the Periodic Table, as traditionally identified, containing the metals rhodium, ruthenium, palladium, osmium, iridium and platinum. The preferred metals from this group are rhodium, palladium and platinum, with platinum being particularly preferred because of its relative availability and particular suitability.

Numerous types of platinum catalysts are known in the art and are disclosed in the patents incorporated by reference hereinabove. They include, for example, reaction products of chloroplatinic acid with olefins, alcohols, ethers, aldehydes and vinylsiloxanes such as tetramethyldivinyldisiloxane. A reaction product of chloroplatinic acid with tetramethyldivinyldisiloxane in the presence of sodium bicarbonate as disclosed in U.S. Pat. No. 3,775,452, dissolved in xylene to a level of about 5% by weight platinum, is often preferred; it is hereinafter designated "Karstedt's catalyst".

Alcoholysis of the chlorine atoms bonded to silicon may finally be achieved by gradual addition of an alcohol, typically methanol, at a temperature in the range of about 90°–120° C. A suitable organic solvent such as toluene may be employed. Following completion of the alcoholysis reaction, the solvent may be removed by vacuum stripping to yield the bis(bis-silylalkyl) dicarboxylate ester.

The preparation of the esters of this invention is illustrated by the following examples.

EXAMPLE 1

A 50 ml. round-bottomed flask was charged with 6 grams (39.2 mmol.) of fumaryl chloride and 4 grams of a commercially available pyridine-functionalized polystyrene. 1,6-Heptadien-4-ol, 10 grams (89.1 mmol.), was then added dropwise, whereupon an exothermic reaction took place. The mixture was allowed to stand for 24 hours, filtered and vacuum stripped to yield the desired bis(1,6-heptadien- 4-yl) fumarate.

To the crude fumarate was added 5 microliters of Karstedt's catalyst. Trichlorosilane was then introduced in three 13.3 gram portions, with addition of the second and third portions being commenced after refluxing caused by the resulting exothermic reaction had ceased. After trichlorosilane addition was complete, the mixture was heated under reflux for 2 hours after which excess trichlorosilane was removed by vacuum stripping. The product was the desired bis[1,7-bis(trichlorosilyl)hept-4-yl] fumarate.

A three-necked 50 ml. round-bottomed flask was charged with 3 grams of crude bis(bis[1,7-bis(trichlorosilyl)heptyl] fumarate and 10 grams of toluene. The mixture was heated to reflux and 11.8 grams (369 mmol.) of methanol was added slowly over 2 hours through a plastic tube extending into the bottom of the flask. The solvent was then removed by vacuum stripping to yield the desired bis[1,7-bis(3-trimethoxysilyl)heptyl] fumarate. Its structure was confirmed by proton nuclear magnetic resonance spectroscopy.

As previously mentioned, the bis(bis-silylalkyl) dicarboxylate esters of this invention are useful as adhesion promoters in addition curable silicon compositions. Said compositions comprise reagents A, B and C as previously defined, in combination with reagent D, the adhesion promoter.

Both one-part and two-part addition curable compositions are included as part of the invention. One-part compositions generally include reagents A–D in combination with inhibitors which suppress curing at ambient temperature; suitable inhibitors are disclosed hereinafter. In two-part compositions, the hydrosilylation catalyst is separated from any combination of reagents A and B prior to the time curing is desired.

Reagent A is at least one polyorganosiloxane having alkenyl, most often $C_{1-3}$ alkenyl and preferably vinyl groups, bonded to silicon. Such silicone materials are well known in the art and have been employed previously in the preparation of cured silicone materials. They are described, for example, in U.S. Pat. Nos. 4,418,157, 4,851,452 and 5,011,865, the disclosures of which are incorporated by reference herein.

A typical linear (polydiorganosiloxane) silicone material useful as reagent A is represented by the formula

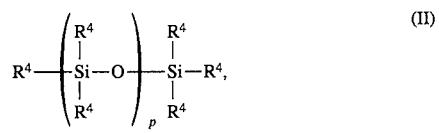

wherein each $R^4$ is independently $C_{1-6}$ alkyl, phenyl, 3,3,3-trifluoropropyl or vinyl and p has a value such that the viscosity of the silicone is in the range of about 100–1,000,000 and preferably about 3,000–95,000 centipoise at 25° C. Most often, each $R^5$ that is not vinyl is methyl.

An art-recognized convention for designating silicone structural units in accordance with the number of oxygen atoms attached to silicon is employed herein. That convention uses the letters M, D, T and Q to designate said number of oxygen atoms as abbreviations for "mono", "di", "tri" and "quatro". Thus, the silicone of formula III consists of M end groups and D internal units. The presence of T and/or Q units imparts branched and/or crosslinked structure to the compound.

As further used herein, expressions such as "M(vinyl)" and "D(hydrogen)" denote an appropriate unit respectively having one vinyl group or one hydrogen atom attached to silicon. Generically, however, proportions of M (etc.) units include such analogous units as M(vinyl). The particularly preferred silicones of formula I are those in which the vinyl groups are attached to terminal silicon atoms.

The proportion of M, D, T and Q units in reagent A and in the mixture as a whole may be varied to afford a composition of the desired degree of branching and other properties. Thus, for example, the aforementioned U.S. Pat. No. 4,418,157 describes a base silicone material which may contain vinyl groups bonded to silicon and which has prescribed proportions of M, D and Q units.

For the purposes of the present invention and especially for use as a conformal coating composition, it is often preferred that at least about 10% and preferably about 25–40% by weight of reagent A comprise compounds with a high proportion of Q units. More specifically, the ratio of combined M and D units (including vinyl- and hydrogen-substituted units) to Q units in such compounds is at most about 0.75:1 and preferably about 0.3–0.7:1. Most preferably, only M and Q units are present. Compounds having these proportions have sufficient crosslinking and/or branching to serve adequately as conformal coatings. Such compounds may be prepared by art-recognized methods, such as the reaction of a silica hydrosol with an alkyl silicate or alkylchlorosilane containing one or more alkyl groups per molecule.

In general, reagent A comprises principally or, preferably, entirely compounds in which vinyl groups are bonded to terminal silicon atoms on the silicone chain.

Reagent B may be represented by a linear polysiloxane of the formula

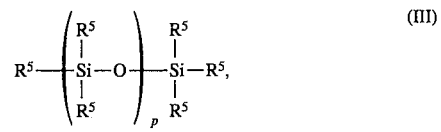

wherein each $R^5$ is independently $C_{1-6}$ alkyl, phenyl, 3,3,3-trifluoropropyl or hydrogen, the hydrogen comprising about 0.3–2.0% by weight thereof. The polysiloxane of formula III comprises M and D units, but reagent B may also typically contain Q units.

Most often, reagent B has an average of no more than one hydrogen atom bonded to any silicon atom and any nonhydrogen $R^5$ values are methyl. It usually contains about 0.02–1.6% (by weight) silicon-bonded hydrogen.

Reagent C is at least one platinum group catalyst as previously defined.

The addition curable compositions of this invention may contain other constituents such as fillers and inhibitors which suppress premature curing. Suitable fillers include extending fillers such as quartz, aluminum oxide, aluminum silicate, zirconium silicate, magnesium oxide, zinc oxide, talc, diatomaceous earth, iron oxide, calcium carbonate, clay, titania, zirconia, mica, ground glass, glass fiber, sand, carbon black, graphite, barium sulfate, zinc sulfate, wood flour, cork and fluorocarbon polymer powder. Also included are reinforcing fillers such as fumed silica and precipitated silica, particularly silica which has been treated with an organohalosilane, a disiloxane and/or a disilazane.

Inhibitors include volatile materials, non-volatile materials or both. Illustrative non-volatile inhibitors are esters of olefinic dicarboxylic acids, as illustrated by dibutyl maleate. Various acetylenic alcohols such as methylbutynol and dimethylhexynol may be used as volatile inhibitors.

In general, about 1–20 parts by weight of reagent B are present in the compositions of this invention per 100 parts of reagent A, which is the basis for all proportions not otherwise defined herein. Reagent C, the hydrosilylation catalyst, is present in a catalytic amount, typically at least about 0.1 and most often about 5–100 ppm of platinum group metal. Reagent D is present in an adhesion promoting amount, most often about 0.3–2.0 parts. Reinforcing and extending fillers, when present, are typically in an amount up to about 50 parts and about 200 parts, respectively. In the case of compositions in which reagent A does not contain a substantial proportion of Q units, the presence of the reinforcing filler may be mandatory.

The compositions of this invention may be prepared by simply blending the constituents. If a two-part composition is desired, one part contains the hydrosilylation catalyst and the other part contains all of either reagent A or, usually, reagent B. Inhibitors are present in one-part compositions and may also be present in two-part compositions, typically in the amount of about 0.01–2.0 parts per 100 parts of reagent A.

The compositions of this invention may be applied to a substrate, typically metal or plastic, by conventional methods such as roller coating, extrusion, brush coating or the like. It is generally preferred to clean the substrate before application of the composition, typically by treatment with aqueous base or a solvent in the case of plastic substrates and with a conventional cleaner in the case of metals.

The preparation and use of the addition curable compositions of this invention is illustrated by the following examples.

EXAMPLE 2

One-part formulations were prepared by blending 10.4 grams of a polydimethylsiloxane having terminal vinyl-containing units and a viscosity of about 80,000 centipoise, 2.6 grams of fumed silica treated with hexamethyldisilazane and octamethylcyclotetrasiloxane, 2.7 microliters of Karstedt's catalyst, 0.152 gram of the product of Example 1 and 0.23 gram of a polymethylsiloxane having about 0.8% silicon-hydrogen bonds. The mixtures were degassed by two cycles of evacuation and centrifugation.

Substrates of aluminum or a commercially available polyetherimide prepared by the reaction of m-phenylenediamine with 2,2-bis[4-(3,4-dicarboxyphenoxy)phenyl] propane dianhydride were cleaned by treatment with a conventional abrasive cleaner (for aluminum) or with 5M aqueous potassium hydroxide for 5 minutes at 70° C. (for polyetherimide), after which they were spatula-coated with the one-pad composition for preparation of lap shear specimens. The specimens were cured by heating for one hour at 70° C. and tested in accordance with ASTM method D3983. Comparison was made with controls in which the adhesion promoter was bis(3-trimethoxysilyl)propyl fumarate.

The lap shear strengths of the compositions of this invention when employed on aluminum and polyetherimide were 14.8 and 24.6 kg/cm², respectively. The controls did not cure under the same conditions. Thus, the effectiveness of the esters of this invention to promote adhesion under low temperature cure conditions is established.

What is claimed is:

1. An addition curable composition comprising a mixture of:

(reagent A) at least one polyorganosiloxane having alkenyl groups bonded to silicon;

(reagent B) at least one hydride polyorganosiloxane comprising at least one organosiloxane unit having an Si—H moiety;

(reagent C) as a catalyst, at least one platinum group metal compound in an amount effective to cause hydrosilylation of reagent A with reagent B; and (reagent D) an adhesion promoting proportion of a bis-(bis-silylalkyl) dicarboxylate ester having the formula

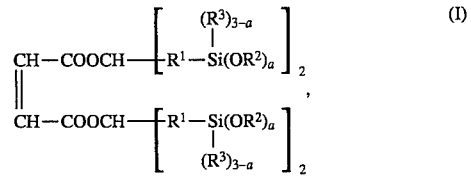

wherein $R^1$ is $C_{2-6}$ alkylene, each of $R^2$ and $R^3$ is independently $C_{1-8}$ alkyl and a is from 1 to 3, said ester being the cis- or trans-isomer or a mixture thereof.

2. A composition according to claim 1 wherein the alkenyl groups are vinyl groups.

3. A composition according to claim 2 wherein reagents A and B are polymethylsiloxanes.

4. A composition according to claim 3 wherein the platinum group metal is platinum.

5. A composition according to claim 3 which is a one-part composition.

6. A composition according to claim 5 wherein reagent A comprises a polymethylsiloxane comprising M and D units and having vinyl groups attached to the terminal silicon atoms.

7. A composition according to claim 5 which also contains a reinforcing filler.

8. A composition according to claim 2 which is a two-part composition.

9. A composition according to claim 2 wherein $R^1$ is trimethylene.

10. A composition according to claim 9 wherein each $R^2$ and each $R^3$ is methyl.

11. A composition according to claim 10 wherein a is 3.

12. A composition according to claim 11 wherein reagent D is a fumarate.

13. An article comprising a metal or plastic substrate having a coating of an addition curable composition comprising a mixture of:

(reagent A) at least one polyorganosiloxane having alkenyl groups bonded to silicon;

(reagent B) at least one hydride polyorganosiloxane comprising at least one organosiloxane unit having an Si—H moiety;

(reagent C) as a catalyst, at least one platinum group metal compound in an amount effective to cause hydrosilylation of reagent A with reagent B; and (reagent D) an adhesion promoting proportion of a bis-(bis-silylalkyl) dicarboxylate ester having the formula

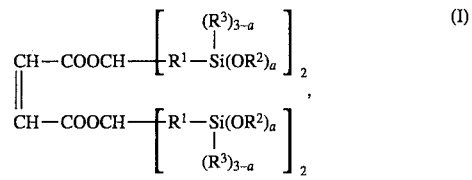

wherein $R^1$ is $C_{2-6}$ alkylene, each of $R^2$ and $R^3$ is independently $C_{1-8}$ alkyl and a is from 1 to 3, said ester being the cis- or trans-isomer or a mixture thereof.

* * * * *